US012434013B2

(12) United States Patent
Dasbach et al.

(10) Patent No.: US 12,434,013 B2
(45) Date of Patent: Oct. 7, 2025

(54) INJECTION DEVICE

(71) Applicant: Sanofi, Paris (FR)

(72) Inventors: Uwe Dasbach, Frankfurt am Main (DE); Alex Zuyev, Bridgewater, NJ (US); Thomas Mark Kemp, Melbourn Herts (GB); Hugo Revellat, Melbourn Herts (GB); Timothy Denyer, Melbourn Herts (GB)

(73) Assignee: Sanofi, Paris (FR)

( * ) Notice: Subject to any disclaimer, the term of this patent is extended or adjusted under 35 U.S.C. 154(b) by 1196 days.

(21) Appl. No.: 17/282,978

(22) PCT Filed: Oct. 9, 2019

(86) PCT No.: PCT/EP2019/077333
§ 371 (c)(1),
(2) Date: Apr. 5, 2021

(87) PCT Pub. No.: WO2020/074570
PCT Pub. Date: Apr. 16, 2020

(65) Prior Publication Data

US 2021/0346608 A1 Nov. 11, 2021

(30) Foreign Application Priority Data

Oct. 12, 2018 (EP) .................................... 18306346

(51) Int. Cl.
*A61M 5/32* (2006.01)
*A61M 5/31* (2006.01)

(52) U.S. Cl.
CPC ........ *A61M 5/3204* (2013.01); *A61M 5/3146* (2013.01); *A61M 2005/3215* (2013.01); *A61M 2207/00* (2013.01)

(58) Field of Classification Search
CPC .............. A61M 5/3204; A61M 5/3146; A61M 2005/3215; A61M 2207/00
(Continued)

(56) References Cited

U.S. PATENT DOCUMENTS 7,771,397 B1 * 8/2010 Olson ................ A61M 5/3202 604/263

FOREIGN PATENT DOCUMENTS

CN 101827623 9/2010
CN 103764207 4/2014
(Continued)

OTHER PUBLICATIONS

PCT International Search Report and Written Opinion in International Appln No. PCT/EP2019/077333, dated Nov. 12, 2019, 10 pages.

(Continued)

*Primary Examiner* — Phillip A Gray
(74) *Attorney, Agent, or Firm* — Fish & Richardson P.C.

(57) ABSTRACT

An injection device comprising a housing and a cap at a distal end of the housing, the cap comprising: an outer member; an intermediate member disposed within the outer member, at least one of the intermediate member or outer member being rotatable relative to the other of the intermediate member or outer member; and, an inner member disposed within the intermediate member, and coupled to at least one of the outer member and the intermediate member, the inner member being configured to engage a needle shield in the housing. The injection device further comprises a lifting mechanism to reduce a force required to remove the cap from the housing, the lifting mechanism comprising at least one axially-inclined portion in engagement with at least one lifting portion such that rotational movement of the (Continued)

outer member or intermediate member is converted into an axial movement of the inner member from the housing.

20 Claims, 11 Drawing Sheets

(58) Field of Classification Search
USPC .......................................................... 604/263
See application file for complete search history.

(56) References Cited

FOREIGN PATENT DOCUMENTS

| | | |
|---|---|---|
| EP | 2175917 | 4/2010 |
| JP | 2007-518507 | 7/2007 |
| WO | WO 2005/070481 | 8/2005 |
| WO | WO 2009/019440 | 2/2009 |
| WO | WO 2013/006119 | 1/2013 |

OTHER PUBLICATIONS

PCT International Preliminary Report on Patentability in International Appln No. PCT/EP2019/077333, dated Apr. 8, 2017, 8 pages.

* cited by examiner

INJECTION DEVICE

CROSS REFERENCE TO RELATED APPLICATIONS

The present application is the national stage entry of International Patent Application No. PCT/EP2019/077333, filed on Oct. 9, 2019, and claims priority to Application No. EP 18306346.0, filed on Oct. 12, 2018, the disclosures of which are incorporated herein by reference.

TECHNICAL FIELD

The present disclosure relates to an injection device with a removable cap and a method of assembling the cap of said injection device

BACKGROUND

Injection devices, such as auto-injectors, are known in the art for dispensing a medicament to the injection site of a patient. Such injection devices typically comprise a housing and a cap. A needle syringe is located in the housing and is sometimes covered by a needle shield. The cap and needle shield are removably attached to the housing to shield the needle of the needle syringe. To dispense the medicament, the cap and needle shield are first removed from the housing to expose the needle. The needle is then inserted into the body of the patient at the injection site to inject the medicament.

The force required to remove the cap from the housing can be relatively high which can be due to the frictional interface between the needle shield and the syringe. Infirm patients such as the elderly or physically impaired may find removing the cap difficult due to the relatively high forces required. Furthermore the force required to remove the cap can be increased further by cold temperatures; some medicaments and therefore some injection devices need to be stored in the fridge at low temperatures. This can exacerbate the difficulty in removing the cap from the housing.

SUMMARY

According to the disclosure there is provided an injection device comprising an elongate housing having a central axis and a cap provided at a distal end of the housing, the cap being removable from the housing and comprising: an outer member for a user to grip when removing the cap from the housing; an intermediate member disposed substantially within the outer member, at least one of the intermediate member or outer member being rotatable relative to the other of the intermediate member or outer member; and, an inner member disposed substantially within the intermediate member and coupled to at least one of the outer member and the intermediate member, the inner member being configured to engage a needle shield of a syringe of medicament when such syringe is received in the housing, wherein the injection device further comprises a lifting mechanism configured to reduce a force required to remove the cap and an engaged needle shield from the housing, the lifting mechanism comprising at least one axially-inclined portion in engagement with at least one lifting portion such that rotational movement of the outer member or intermediate member is converted into an axial movement of the inner member in a distal direction from the housing.

According to the disclosure there is also provided an injection device comprising an elongate housing having a central axis and a cap provided at a distal end of the housing, the cap being removable from the housing and comprising: an outer member for a user to grip when removing the cap from the housing; an intermediate member disposed substantially within the outer member, at least one of the intermediate member or outer member being rotatable relative to the other of the intermediate member or outer member; an inner member disposed substantially within the intermediate member and coupled to at least one of the outer member and the intermediate member, the inner member being configured to engage a needle shield of a syringe of medicament when such syringe is received in the housing, and a lifting mechanism configured to reduce a force required to remove the cap and an engaged needle shield from the housing, the lifting mechanism comprising at least one axially-inclined portion in engagement with at least one lifting portion such that rotational movement of the outer member or intermediate member is converted into an axial movement of the inner member in a distal direction from the housing.

Advantageously the lifting mechanism can assist a user in removing the cap from the housing, therefore requiring less force from the user to remove the cap, relative to the force required without assistance. Infirm patients such as the elderly or physically impaired may find removing the cap difficult, so a reduction in the force required to remove the cap from the housing is beneficial. Furthermore if the injection device has been stored at low temperatures this can cause the required force to remove the cap from the housing to increase relative to the force required for removal of the cap at room temperature. This can cause further problems to those who already find removing the cap difficult.

The outer member can include a lid and the lid and the outer member can be separate components, the lid being fixed rotationally and axially to the outer member. However, it can be appreciated that the lid and the outer member could also be formed as a single component. Manufacturing the components as separate parts can enable a simpler assembly process, however manufacturing them as one component enables a reduction in the overall number of components in the device.

The outer member can include a lid and the inner member can comprise an aperture at a distal end. The aperture can be in engagement with a fixing portion on the lid such that the inner member is coupled to the lid so as to be fixed axially with respect to the lid and to be rotatable with respect to the lid. In addition or alternatively the outer member may comprise an annulus shaped portion which can be in engagement with clips on a distal end of the inner member such that the inner member is fixed axially with respect to the outer member and rotatable with respect to the outer member. Advantageously the inner member being rotatable to the outer member can mean that the needle shield is not rotated when the cap is removed. Rotation of the needle shield, while in situ covering the needle of a syringe, could damage the needle for example by coring.

The intermediate member and inner member may comprise a stop mechanism, the inner member is free to move axially in a distal direction with respect to the intermediate member until a first stop portion of the intermediate member engages with a second stop portion of the inner member such that the inner member is prevented from further axial movement relative to the intermediate member. The stop mechanism can prevent rotational movement of the inner member relative to the intermediate member. An advantage of this feature is that the intermediate portion is not axially fixed to the inner member until the stop portions are engaged, this enables the inner member to move the needle shield in a distal direction independently of the intermediate member, the components are then fixed axially for the final lift of the cap from the housing.

The axially-inclined portion can be a groove or cut out and the lifting portion can be a boss, the lifting portion is located substantially within the axially-inclined portion, wherein as the outer member is twisted the lifting portion is forced to follow a path of the axially-inclined portion, causing axial movement of the outer member and the inner member.

The axially-inclined portion can be a ridge or projection and the lifting portion can be a boss, the lifting portion is axially offset from the axially-inclined portion but in contact with a distal or proximal edge of the axially-inclined portion, wherein as the outer member is twisted the lifting portion is forced to follow a path of the axially-inclined portion causing axial movement of the outer member and the inner member in a distal direction.

An advantage of this is that a simple mechanism which is easy to manufacture and assemble enables a momentum build up to assist a user in removing a cap or needle shield from an injection device.

The axially inclined portion may be a first axially inclined portion located on one of an outer face of the intermediate member and an inner face of the outer member, and the lifting portion can be a first lifting portion on the other of the outer face of the intermediate member or the inner face of the outer member, the outer face being directed away from a central axis of the injection device and the inner face being directed towards a central axis of the injection device.

The lifting mechanism may comprise a second lifting portion and a second axially-inclined portion, the second lifting portion being located on one of an inner face of the intermediate member and an outer face of the inner member and the second axially-inclined portion being on the other of the outer face of the inner member and the inner face of the intermediate member, an outer face being directed away from a central axis of the injection device and an inner face being directed towards a central axis of the injection device. The second axially-inclined portion may have a shallower gradient with respect to the axial direction than the first axially-inclined portion.

Advantageously the intermediate member comprising two lifting portions enables a pulling force of the outer member to be converted into a twisting movement of the intermediate member and in turn an axial movement of the inner member to provide a mechanical advantage when removing the cap and the needle shield of the injection device. Furthermore the difference in gradients can enable a greater axial movement of the outer member to cause a smaller axial movement of the inner member relative to the axial movement of the outer member. The difference in gradients could also enable a smaller axial movement of the outer member to cause a larger axial movement of the inner member relative to the movement of the outer member if the first axially inclined portion has a shallower gradient with respect to the axial direction than the second axially inclined portion. Furthermore the axial force on the inner member can be reduced or increased relative to the axial force applied to the outer member based on the difference in gradients of the first and second axially inclined portions.

At least one of the axially inclined portions can be a groove or cut out and at least one of the lifting portions can be a boss, the at least one of the lifting portions is located substantially within the at least one of the axially-inclined portions, wherein as the outer member is lifted in a distal direction from the housing each lifting portion is forced to follow a path of each axially-inclined portion, causing rotational movement of the intermediate member and axial movement of the inner member.

At least one of the axially-inclined portions can be a ridge or projection and at least one of the lifting portions can be a boss, the at least one of the lifting portions is axially offset from the at least one of the axially-inclined portions but in contact with a distal or proximal edge of the at least one of the axially-inclined portions, wherein as the outer member is lifted in a distal direction away from the housing each lifting portion is forced to follow a path of each axially-inclined portion, causing rotational movement of the intermediate member and axial movement of the inner member.

An advantage of this is that a simple mechanism which is easy to manufacture and assemble enables a momentum build up to assist a user in removing a cap from an injection device.

The injection device may comprise a holding portion at one end of the axially-inclined portion or the second axially-inclined portion to engage with the lifting portion, wherein when the holding portion and the lifting portion are engaged the cap and the housing are held together and relative movement of the cap and the housing is resisted. It may be required that the cap is pushed in a proximal direction to release the lifting portion from the holding portion before removal of the cap. An advantage of this is that premature removal of the cap is prevented, this feature may also prevent movement of particular components of the device during storage or transport which could damage the device.

According to one aspect of the disclosure there is provided an injection device comprising: an elongate housing having a central axis and a cap provided at a distal end of the housing, the cap being removable from the housing and comprising: an outer member for a user to grip when removing the cap from the housing; and an inner member disposed substantially within the outer member, and coupled to the outer member such that the outer member is rotatable with respect to the inner member, the inner member being configured to engage a needle shield of a syringe of medicament when such a syringe is received in the housing; and a lifting mechanism configured to reduce a force required to remove the cap and an engaged needle shield from the housing, the lifting mechanism comprising: a lifting portion on one of the outer member and the housing, and an axially-inclined portion on the other of the outer member and the housing, wherein, the lifting portion engages with the axially-inclined portion such that rotational movement of the outer member with respect to the housing is converted into an axial movement of the inner member in a distal direction from the housing.

Advantageously the lifting mechanism can assist a user in removing the cap from the housing, therefore requiring less force from the user to remove the cap, relative to the force required without assistance. Infirm patients such as the elderly or physically impaired may find removing the cap difficult, so a reduction in the force required to remove the cap from the housing is beneficial. Furthermore if the injection device has been stored at low temperatures this can cause the required force to remove the cap from the housing to increase relative to the force required for removal of the cap at room temperature. This can cause further problems to those who already find removing the cap difficult.

The lifting portion can be a protrusion on the outer member extending axially in a proximal direction from a proximal edge of the outer member, the axially-inclined portion being on the housing. Alternatively the lifting portion can be a protrusion on the housing extending axially in a distal direction from a distal edge of the housing, the axially-inclined portion being on the outer member. Alternatively the lifting portion can be an inwardly protruding boss on an inner surface of the outer member, extending towards the central axis of the housing, the axially-inclined portion being on the housing. Alternatively the lifting portion can be an outwardly protruding boss on an outer surface of the housing, extending away from the central axis of the housing, the axially-inclined portion being on the outer member.

The axially-inclined portion can be a recessed portion for engagement with the lifting portion. Alternatively the axially-inclined portion can be a ridge or projection for engagement with the lifting portion. The axially-inclined portion can be curved. Alternatively the axially-inclined portion can be linear. Advantageously the axially inclined portion can be a number of varying profiles and gradients. These can be chosen based on the particular requirements of the injection device, for example but not limited to the required axial movement of the inner member, or the required force reduction in removing the cap for a user.

Before the cap is removed from the housing, the cap can be configured to engage with the housing such that the outer member extends in a distal direction over a proximal end of the housing to cover the lifting mechanism. This protects the lifting mechanism and provides a more aesthetic interface between the cap and the housing.

Before the cap is removed from the housing, the cap can be configured to engage with the housing such that the lifting mechanism is exposed. Advantageously this enables less material to be used in manufacturing the outer member.

The axially-inclined portion can comprise more than one gradient to provide varying levels of assistance in removal of the cap from the housing.

The housing and the outer member can meet at an interface, the housing and the outer member can be non-circular in cross section at this interface, perpendicular to the central axis of the housing. This enables more freedom in the cross-sectional design of the housing and the cap.

The injection device may comprise a syringe having a needle disposed within the housing, wherein said syringe contains a medicament.

The injection device can comprise a needle shield to cover the needle; furthermore the inner member may comprise an engagement member for engagement with the needle shield, wherein removal of the cap simultaneously removes the needle shield. The engagement member can be a grabber, a barb or deflectable arm or may be an alternative known way of fixedly coupling two components together. The engagement member may cut into the needle shield or clamp to the needle shield. The inner member being configured to engage the needle shield can mean that the inner member has a gripper or alternative as described above attached to the inner member, or has an integral part of the inner member to engage the needle shield. It shall be appreciated that infirm patients such as the elderly or physically impaired may find removing the needle shield more difficult than removing the cap due to the small size of the needle shield making it difficult to handle so coupling the two components together for simultaneous removal addresses this issue.

In some embodiments, the at least one axially-inclined portion is in engagement with the at least one lifting portion such that rotational movement of the outer member or intermediate member is converted into said axial movement of the inner member in the distal direction from the housing such that the axial movement of the inner member in the distal direction from the housing urges the engaged needle shield in the distal direction from the housing.

In some embodiments, the needle shield comprises a rigid outer member and a resilient inner member.

In some embodiments, the inner member is coupled to said at least one of the outer member and intermediate member and is configured to engage said at least one of the outer member and the intermediate member.

In some embodiments, the cap comprises the lifting mechanism.

In some embodiments, all of the inner, intermediate and outer members are removable from the housing.

In some embodiments, the intermediate and outer members are removable together from the housing.

There is provided a method of assembling the cap of the injection device comprising the following steps: holding the intermediate member and the inner member in an engaged position, relative to one another; clipping the outer member onto the inner member to form a sub assembly; installing the sub assembly on a housing assembly, the housing assembly including the housing and the needle shield to cover the needle; priming the injection device; and clipping the lid onto the inner member and engaging via a press fit connection with the outer member.

The intermediate member can include a first engagement portion and the outer member can comprise a secondary engagement portion; the method comprising clipping the outer member onto the inner member and the secondary engagement portion of the outer member engaging with the primary engagement portion of the intermediate member.

The outer member can comprise an ergonomic surface comprising a high friction material or formations to enhance the gripping characteristics of the outer member so the cap can be more easily removed by a user. A further advantage is that if the cap has any condensation on it from being stored at cold temperatures it can become slippery and difficult to grip, or if it is still cold can be uncomfortable for a user to grip, the ergonomic surface can address this.

These and other aspects will be apparent from and elucidated with reference to the embodiments described hereinafter.

BRIEF DESCRIPTION OF THE FIGURES

Embodiments will now be described, by way of example only, with reference to the accompanying drawings, in which.

DETAILED DESCRIPTION

Figure 1A:
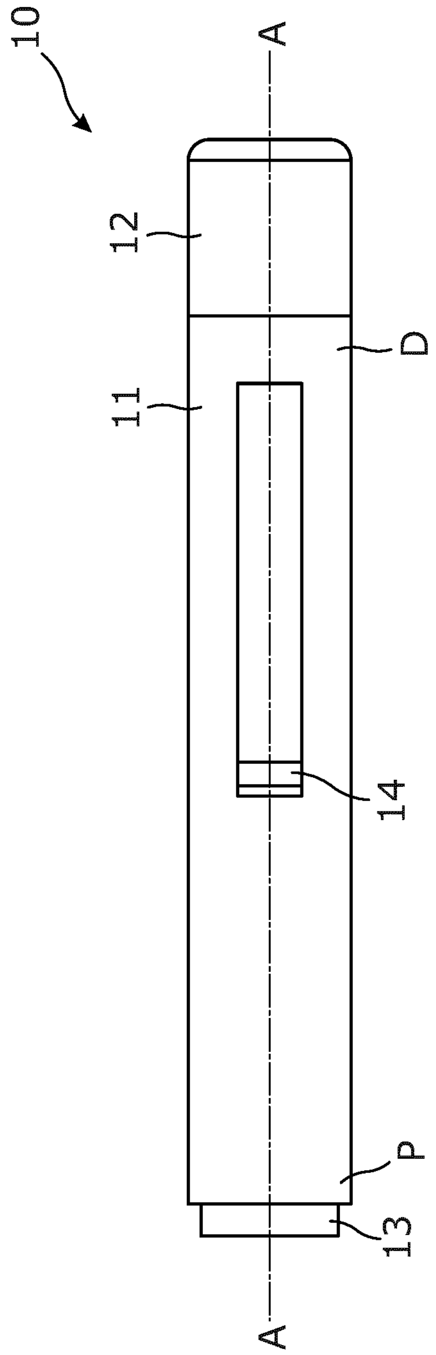
FIG. 1A is a schematic side view of an auto-injector with a cap attached to a housing of the auto-injector.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1B:
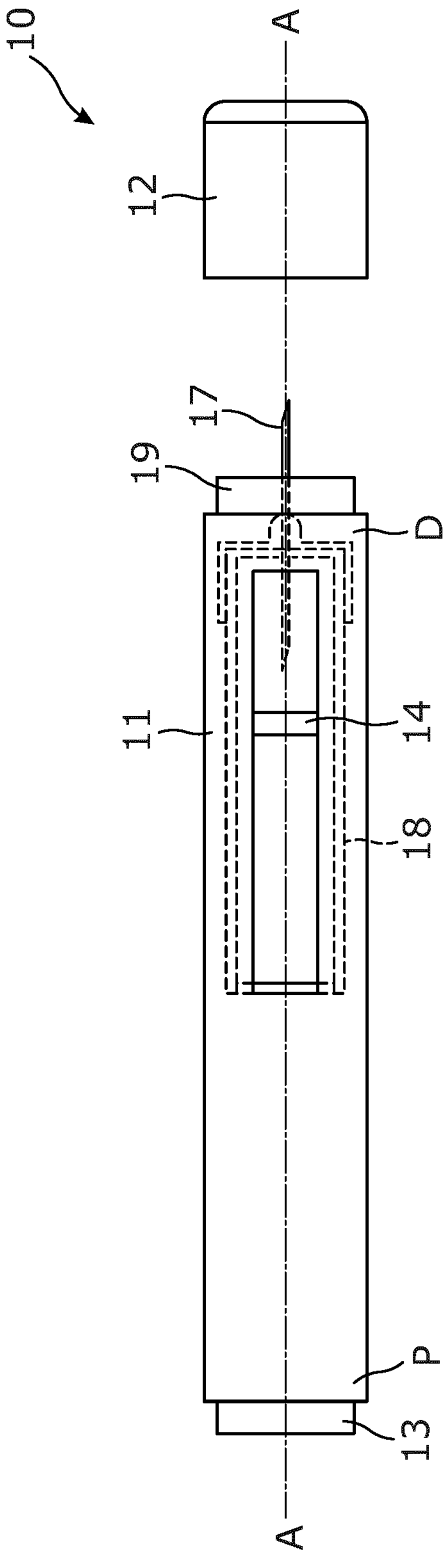
FIG. 1B is a schematic side view of the auto-injector of FIG. 1A, with the cap removed from the housing.

An exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g. a syringe) and the components required to facilitate one or more steps of the delivery process. Device 10 can also include a cap assembly or cap 12 that can be detachably mounted to the housing 11. Typically a user must remove cap 12 from housing 11 before device 10 can be operated.

As shown, housing 11 is substantially cylindrical and has a substantially constant diameter along the longitudinal axis A-A. The housing 11 has a distal region D and a proximal region P. The term "distal" refers to a location that is relatively closer to a site of injection, and the term "proximal" refers to a location that is relatively further away from the injection site.

Device 10 can also include a needle sleeve 19 coupled to housing 11 to permit movement of sleeve 19 relative to housing 11. For example, sleeve 19 can move in a longitudinal direction parallel to longitudinal axis A-A. Specifically, movement of sleeve 19 in a proximal direction can permit a needle 17 to extend from distal region D of housing 11.

Insertion of needle 17 can occur via several mechanisms. For example, needle 17 may be fixedly located relative to housing 11 and initially be located within an extended needle sleeve 19. Proximal movement of sleeve 19 by placing a distal end of sleeve 19 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 19.

Another form of insertion is "automated," whereby needle 17 moves relative to housing 11. Such insertion can be triggered by movement of sleeve 19 or by another form of activation, such as, for example, a button 13. As shown in FIGS. 1A & 1B, button 13 is located at a proximal end of housing 11. However, in other embodiments, button 13 could be located on a side of housing 11.

Other manual or automated features can include drug injection or needle retraction, or both. Injection is the process by which a bung or piston 14 is moved from a proximal location within a syringe 18 to a more distal location within the syringe 18 in order to force a medicament from the syringe 18 through needle 17. In some embodiments, a drive spring (not shown) is under compression before device 10 is activated. A proximal end of the drive spring can be fixed within proximal region P of housing 11, and a distal end of the drive spring can be configured to apply a compressive force to a proximal surface of piston 14. Following activation, at least part of the energy stored in the drive spring can be applied to the proximal surface of piston 14. This compressive force can act on piston 14 to move it in a distal direction. Such distal movement acts to compress the liquid medicament within the syringe 18, forcing it out of needle 17.

Following injection, needle 17 can be retracted within sleeve 19 or housing 11. Retraction can occur when sleeve 19 moves distally as a user removes device 10 from a patient's body. This can occur as needle 17 remains fixedly located relative to housing 11. Once a distal end of sleeve 19 has moved past a distal end of needle 17, and needle 17 is covered, sleeve 19 can be locked. Such locking can include locking any proximal movement of sleeve 19 relative to housing 11.

Another form of needle retraction can occur if needle 17 is moved relative to housing 11. Such movement can occur if the syringe 18 within housing 11 is moved in a proximal direction relative to housing 11. This proximal movement can be achieved by using a retraction spring (not shown), located in distal region D. A compressed retraction spring, when activated, can supply sufficient force to the syringe 18 to move it in a proximal direction. Following sufficient retraction, any relative movement between needle 17 and housing 11 can be locked with a locking mechanism. In addition, button 13 or other components of device 10 can be locked as required.

Figure 2:
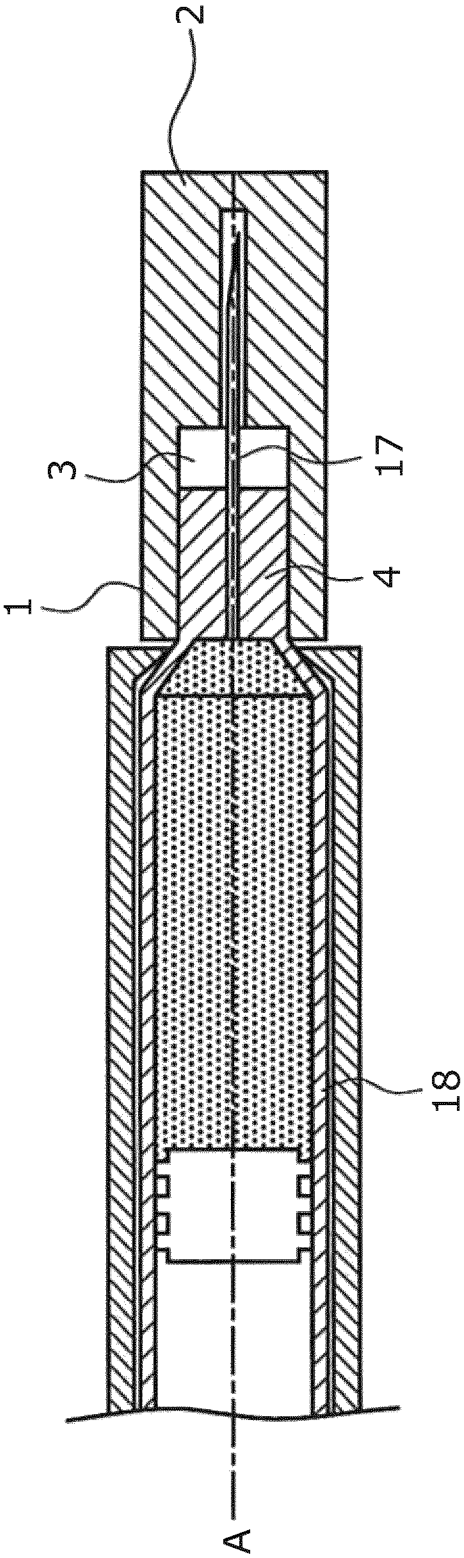
FIG. 2 is a close-up schematic cross-sectional side view of a needle shield of an auto-injector.

Referring now to FIG. 2 an injection device 10 can further comprise a needle shield 1. The needle shield 1 comprises a body 2 of impermeable material with a recess 3 in the proximal end of the body 2. The recess 3 is configured to receive the needle hub 4 and the needle 17 such that the needle 17 is shielded by the body 2. The inside surface of the body 2 and the outside surface of the needle hub 4 frictionally engage to seal the recess 3 to prevent the ingress of air into the recess 3. Thus, the needle 17 is kept sterile when the cap 12 is attached to the housing 11.

It can be advantageous for the cap 12 and the needle shield 1 to be removed simultaneously which makes removal of the cap 12 and needle shield 1 easier for a user. The force required to remove the cap 12 from the injection device 10 can be relatively high such that an elderly or physically impaired user may find removing the cap difficult. One reason this difficulty can arise is due to the frictional engagement between the needle shield 1 and the needle hub 4. However, it can be appreciated that the force required varies based on the materials of construction, the design of the device and the ambient temperature among other variables. Furthermore, the force required to remove the needle shield and the cap can be increased further by cold temperatures. For some medicaments and therefore some injection devices there is a requirement or need to store the device in the fridge or at low temperatures. This can exacerbate the difficulty in removing the cap 12 from the housing 11.

Figure 3:
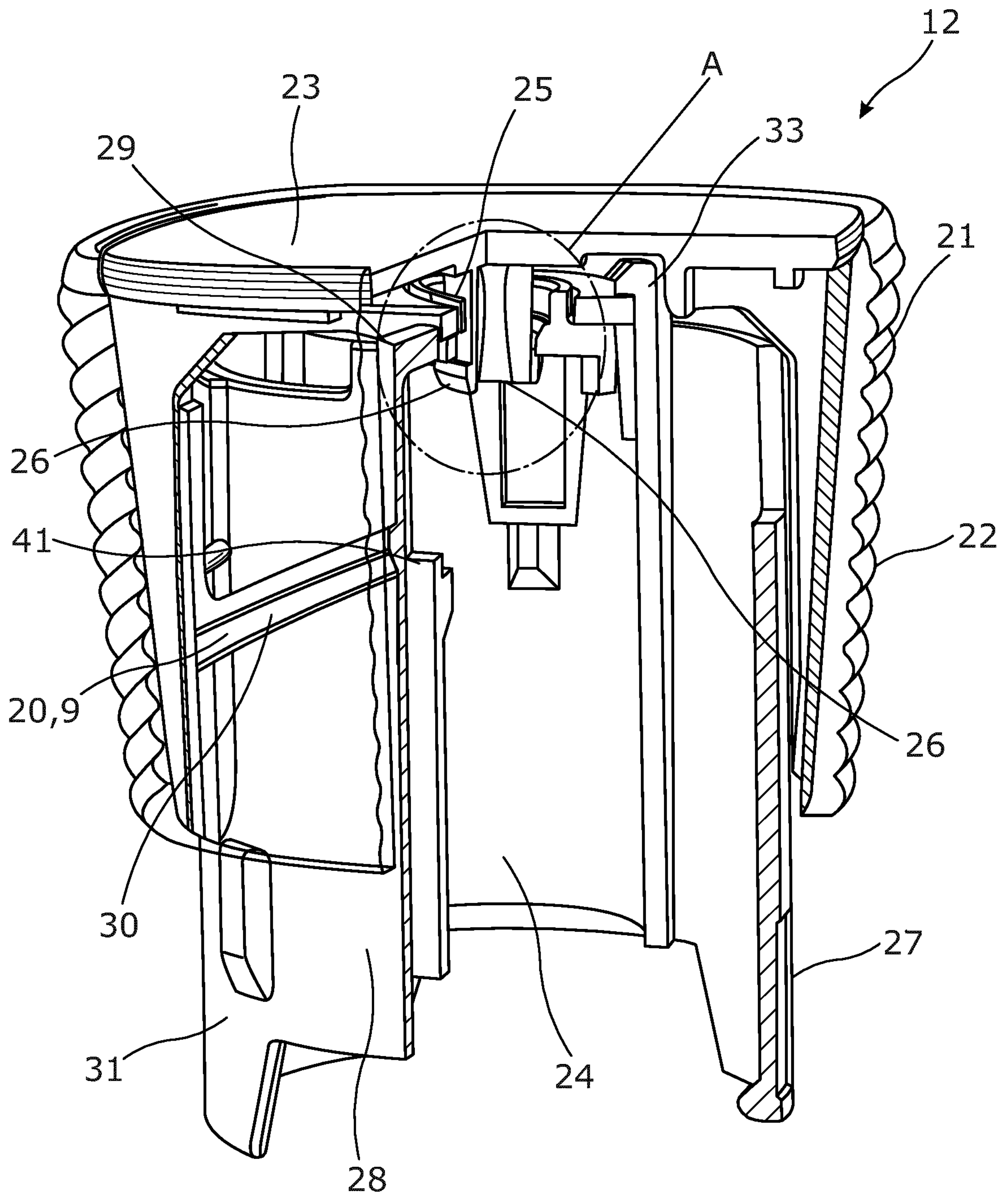
FIG. 3 is a close-up isometric view of a cap according to one aspect showing internal components of the cap.
Figure 4:
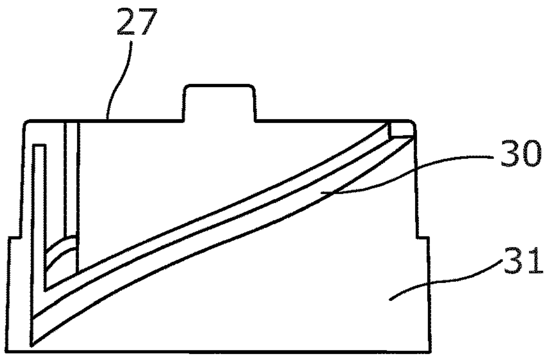
FIG. 4 is a close-up side view of the axially-inclined portion of the intermediate member of FIG. 3.
Figure 5:
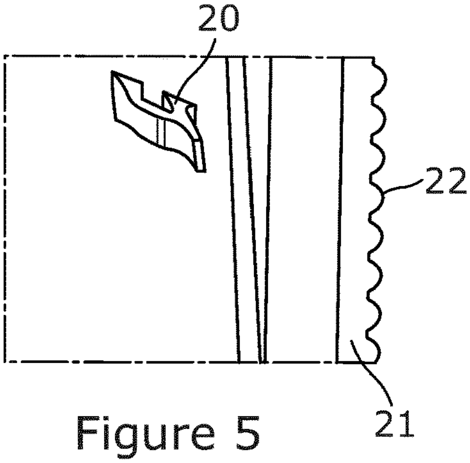
FIG. 5 is a close-up cross-sectional view of the outer member of FIG. 3 showing a lifting portion.
Figure 6:
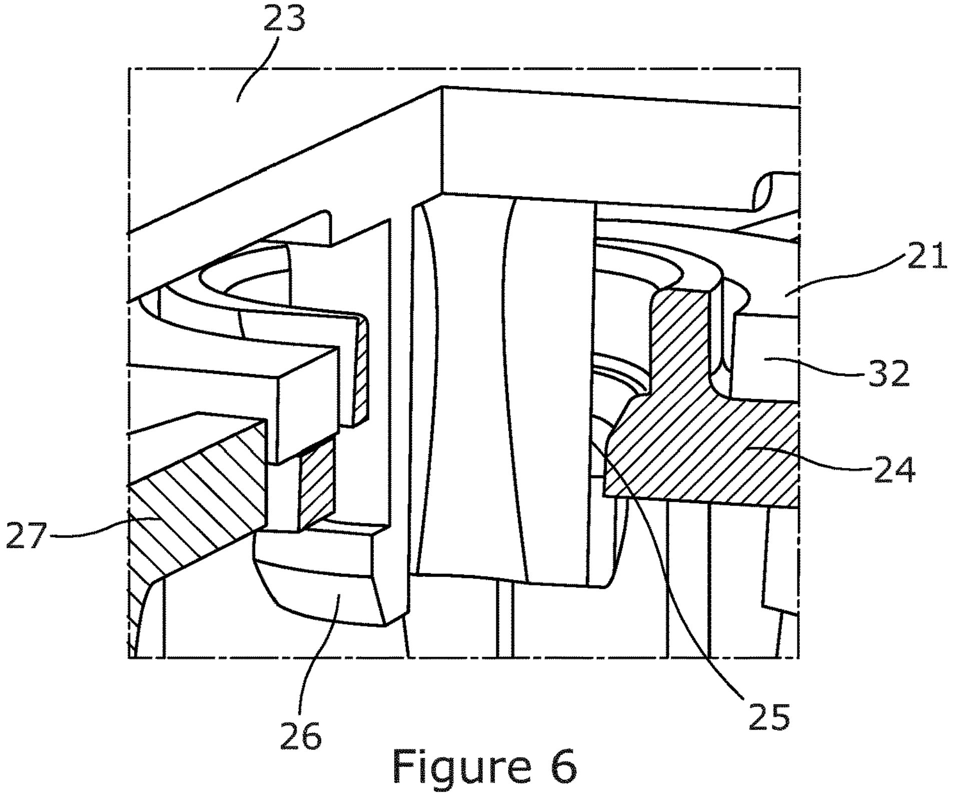
FIG. 6 is a close-up of section A of FIG. 3.
Figure 7:
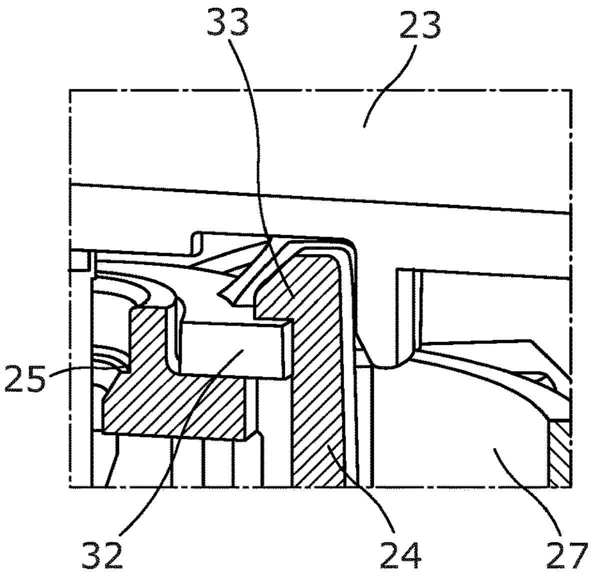
FIG. 7 is a close up view of an inner member clip of FIG. 3.
Figure 8:
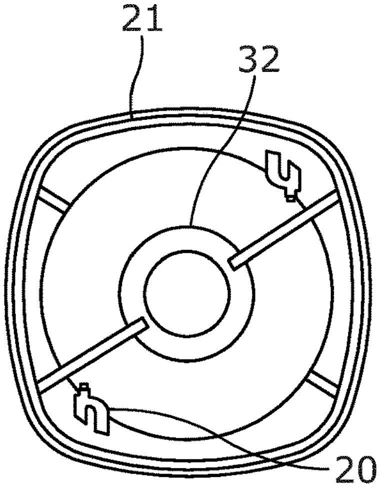
FIG. 8 is a plan view of the outer member of FIG. 3.
Figure 9:
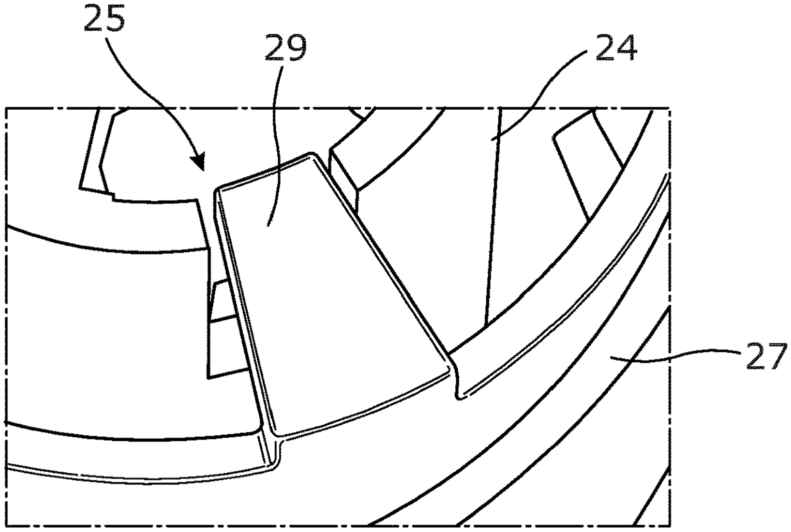
FIG. 9 is a close up isometric top view of the intermediate member and the inner member of FIG. 3.
Figure 10:
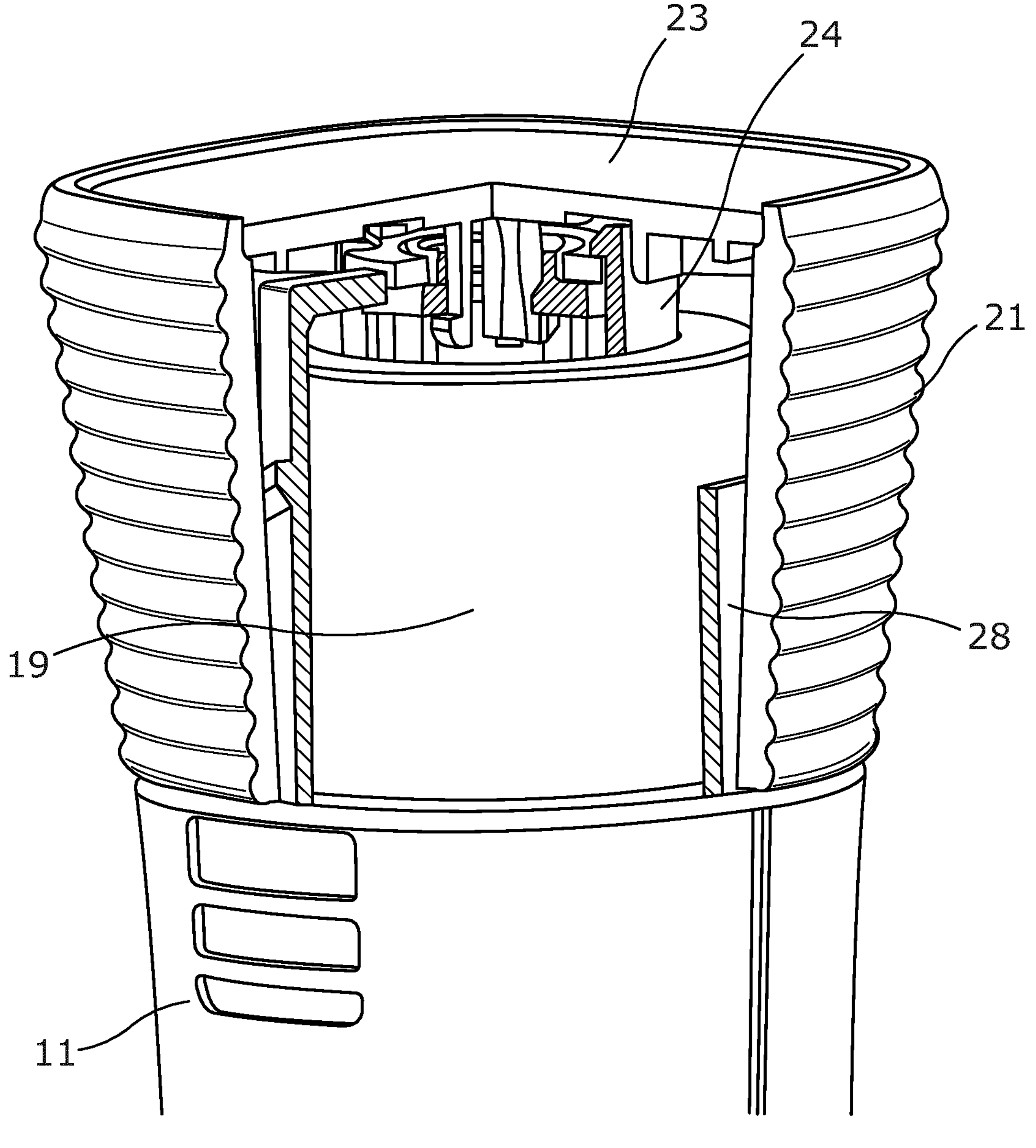
FIG. 10 is the cap of FIG. 3 before it has been removed on an injection device such as those in FIGS. 1A and 1B.
Figure 11:
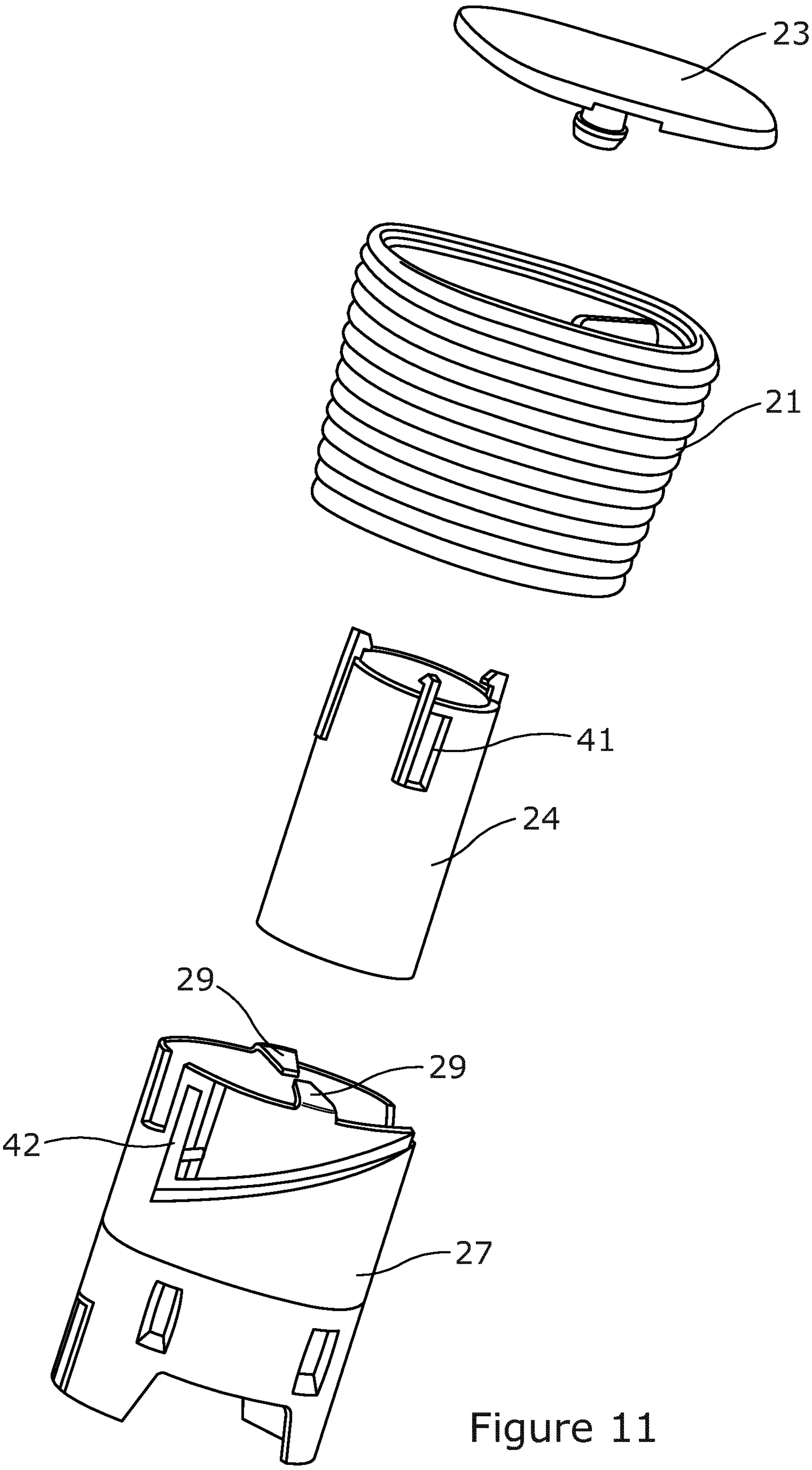
FIG. 11 is an exploded view of the main components of FIG. 3.

Illustrated in FIG. 3, there is a removable cap 12 having an outer member 21 with formations 22 to enhance the gripping characteristics of the outer member 21. It can be appreciated however that the outer member 21 may be made of a higher friction material, it may comprise a further coating, it may be specifically shaped ergonomically, or it may have no friction enhancing properties. The outer member 21 is coupled to a lid 23, the lid can be coupled to the outer member 21 by a press fit connection or alternative known connection means, the outer member 21 and the lid 23 can also be integrally formed so they are one component as they are fixed both axially and rotationally to one another. The outer member 21 comprises a lifting portion 20 which in this instance is an inwardly protruding boss 9. The outer member 21 further comprises an annulus 32.

The removable cap 12 has an inner member 24 with an aperture 25, the lid 23 has clips 26 which engage with the inner member 24 via the central aperture 25. This engagement axially couples the lid 23 to the inner member 24, however allows the lid 23 to rotate with respect to the inner member 24. The inner member 24 further comprises clips 33 which clip onto the annulus 32 of the outer member 21. This axially couples the outer member 21 and inner member 24 but allows them to rotate in relation to one another. The inner member 24 can interface or be configured to engage with the needle shield 1, this can be in the form of but not limited to, grippers, a barb cutting into or sitting tightly against the needle shield 1 or a frictional lock between the inner member 24 and the needle shield 1. The inner member 24 being configured to engage with the needle shield can mean that there is a separate component such as a grabber (not shown) attached or located within the inner member 24 which can further comprise any of the mechanisms described above.

The cap 12 also comprises an intermediate member 27 which is located substantially between the inner member 24 and the outer member 21. The intermediate member 27 has a substantially tubular body 28 with at least one inwardly projecting formation 29 at its distal end. The formation 29 is for engagement with a cut out 41 of the inner member 24, the inwardly projecting formation 29 and cut out 41 providing a stop mechanism. The inner member 24 is free to move axially in a distal direction away from the housing with respect to the intermediate member 27, until a first stop portion (i.e. the inwardly projecting formation 29) of the intermediate member 27 is engaged with a second stop portion (i.e. the proximal most extremity of cut out 41). When the first stop portion is engaged with the second stop portion the inner member 24 is fixed axially to the intermediate member 27. The stop mechanism also rotationally couples the intermediate member 27 to the inner member 24. An advantage of this feature is that the intermediate member 27 is not fixed axially to the inner member 24 until the stop portions are engaged. This enables the inner member 24 to move the needle shield 1 in a distal direction independently of the intermediate member 27 until the stop portions engage, the inner member 24 and intermediate member 27 are then fixed axially for the final lift of the cap from the housing. It can be appreciated that the first stop portion could be a cut out, and the second stop portion could be a projection; furthermore the skilled person can envisage a number of alternative known means for the first and second stop portions which would provide a stopping mechanism as described above.

The intermediate member 27 also comprises an axially inclined portion 30 which is in the form of a ramped groove in an outer wall 31 of the intermediate member. The ramp can be an indent in the outer wall 31, or a cut out the entire way through the intermediate member 27. The ramp is inclined; however it can be appreciated that it can incline in either direction, it may also be a curved shape or comprise more than one gradient. The inclination of the ramp required is dependent on the direction of the rotational movement of the outer member 21 required to remove the cap 12. The intermediate member 27 is also fixed rotationally to the housing 11 which prevents the intermediate member 27 and therefore inner member 24 from rotational movement even when the outer member 21 is twisted or rotated.

It can be appreciated that there a number of ways which would be known to a person skilled in the art to rotationally and axially couple two components to one another. Any combination of grooves, clips, bosses, formations and protrusions can be used to couple each component described above allowing either rotational movement, axial movement or neither depending on the requirements described above. It can also be appreciated that the lifting portion 20 may be located on the intermediate member 27 and the axially-inclined portion 30 may be located on the outer member 21. The first stop portion may be located on the inner member 24, the second stop portion located on the intermediate member 27. The stop portions can also be any known mechanism described above which allows relative axial movement to a point and then prevents relative axial movement past that point.

Figure 12:
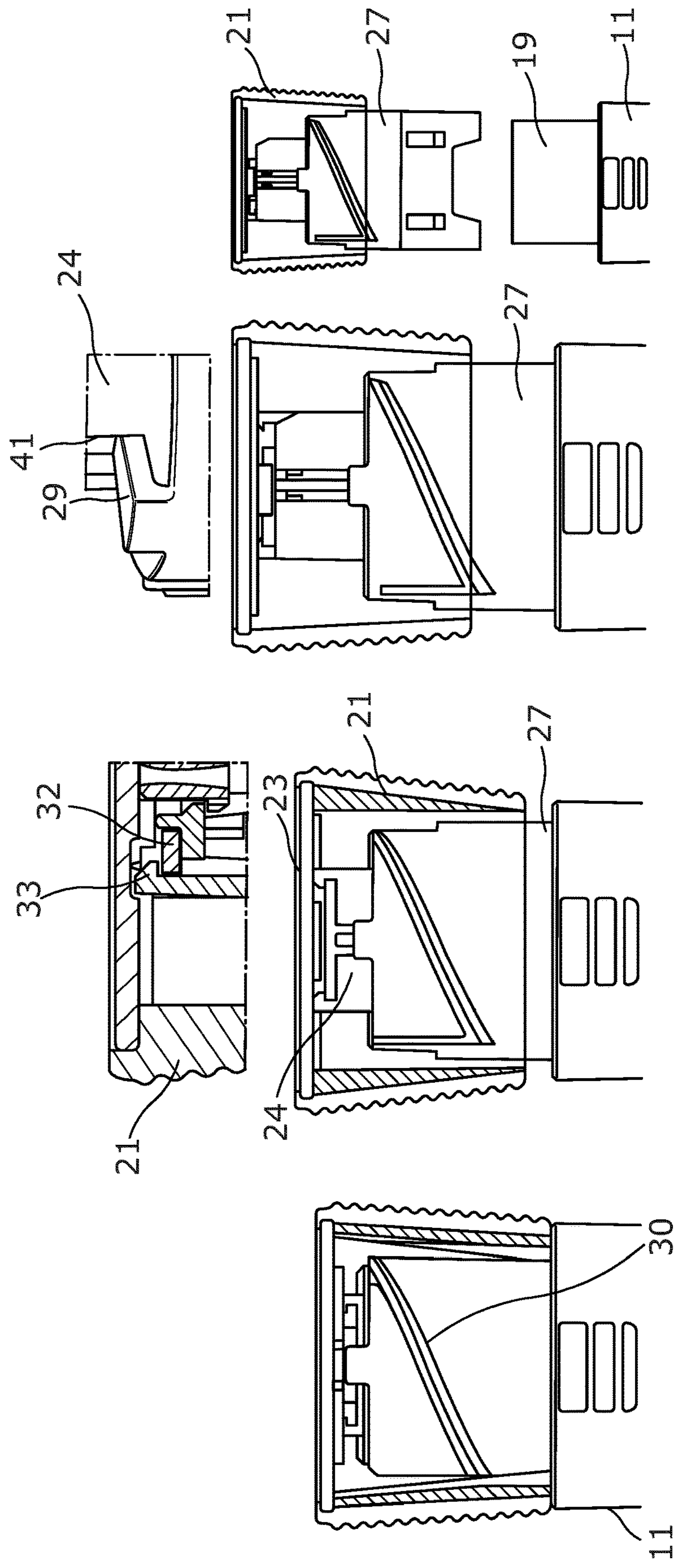
FIG. 12 is a side view showing the outer member as transparent so internal components can be viewed at various stages of removing the cap of FIG. 3.

The mechanism of removal of the cap 12 from the housing 11 can be described as follows and can be seen in the steps shown in FIG. 12. As a user twists or rotates the outer member 21, the force is transmitted from the outer member 21 to the inner member 24 through the clips 33.

The inner member 24 is moved in a distal direction away from the housing 11. The lifting portion 20 travels along the axially-inclined portion 30 from a first position to a second position, i.e. the inwardly protruding boss travels along the ramp as the outer member 21 is twisted. The first position being a proximal most end of the axially inclined portion and the second position being a distal most end of the axially inclined portion. At the end of the ramp, the intermediate member 27 and outer member 21 are fixed axially to one another. The outer member 21 is then lifted, removing the cap with less force than would have been required before twisting of the outer member 21 and more smoothly due to the momentum buildup of the method described above. The injection device 10 may further comprise a needle shield 1 and removal of the cap 12 removes the needle shield 1 simultaneously.

A method of assembling the cap 12 of the injection device includes the following steps. The intermediate member 27 and the inner member 24 are held in position in the assembly equipment. The outer member 21 can then be clipped onto the inner member 24 forming a sub assembly. In some instances the intermediate member 27 incorporates a primary engagement portion which can be for example but not limited to, a thread, protrusion or a groove. The outer member 21 then comprises a secondary engagement portion which can be for example but not limited to a thread, protrusion or a groove to suit the primary engagement portion. The outer member 21 is clipped onto the inner member 24 the secondary engagement portion of the outer member 21 also engages with the primary engagement portion of the intermediate member 27. The sub assembly is installed on a housing assembly, the housing assembly having previously been assembled and including the housing 11 and the needle shield 1 to cover the needle 17. The injection device undergoes a priming action before the lid 23 is clipped onto the inner member 24 and engages via a press fit connection with the outer member 21.

Figure 13:
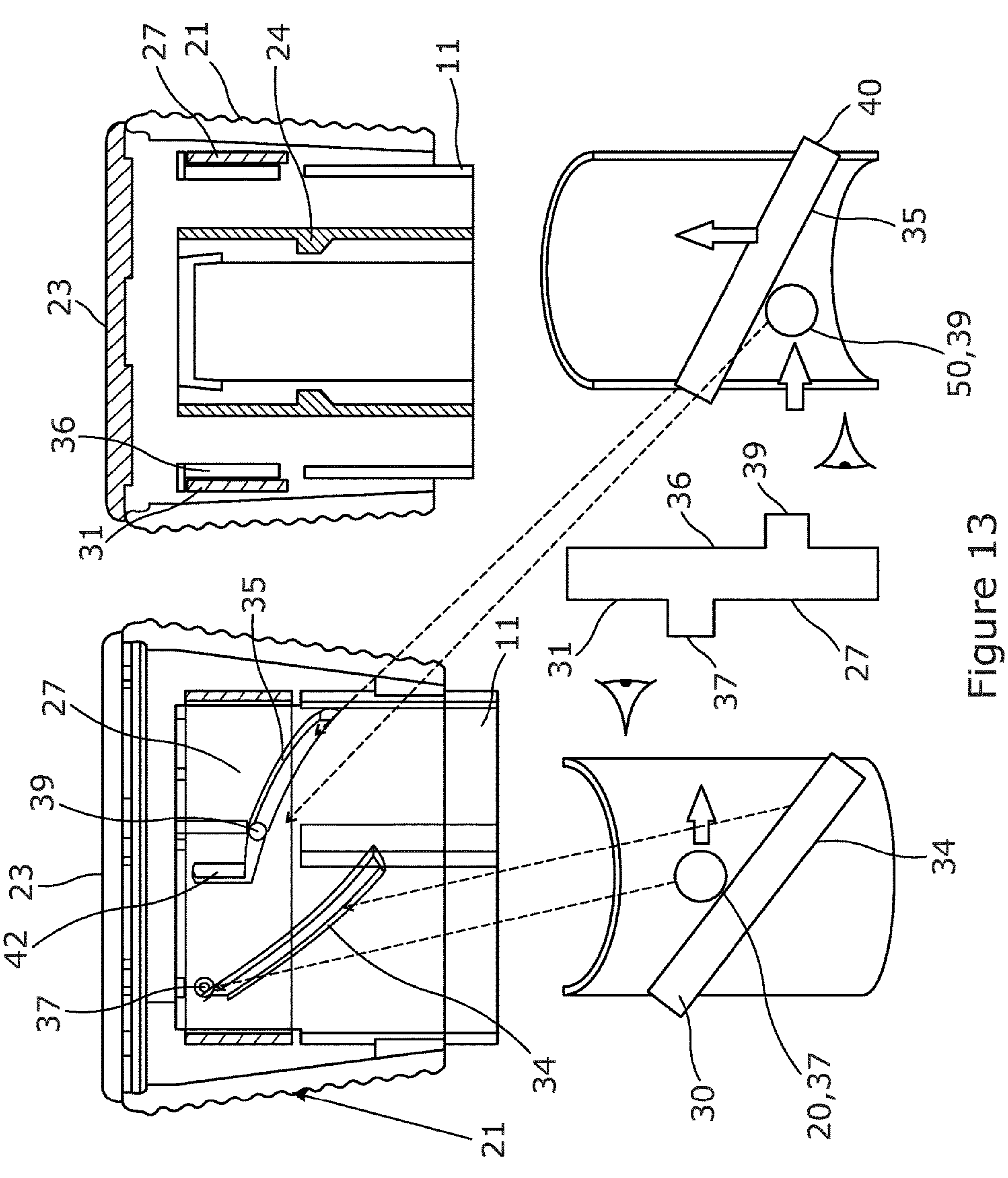
FIG. 13 is a diagrammatic view of a cap according to a second embodiment.

Another embodiment is shown in FIG. 13. A number of the features remain the same as in previous Figures and like components retain the same reference numerals. The intermediate member 27 has a first lifting portion 20 in the form of a primary protruding boss 37 and a second lifting portion 50 in the form of a secondary protruding boss 39. The outer member comprises a first axially-inclined portion 30 in the form of a primary ramp 34 and the inner member comprises a second axially-inclined portion 40 in the form of a secondary ramp 35. It can be appreciated that the ramps 34, 35 can be protruding from the inner or outer member, an indent or groove or a cut out the entire way through the inner or outer member. The ramp is inclined; however it can be appreciated that it can incline in either direction, curve, or comprise more than one gradient.

The primary protruding boss 37 is configured to engage with the primary ramp 34 from a first position to a second position, in the illustrated example from a distal most end of the ramp to a proximal most end of the ramp. The intermediate member 27 is fixed axially to the inner member 24 and not the outer member 21. As the outer member is pulled in a distal direction away from the housing, the intermediate member 27 resists the axial movement due to the engagement with the inner member 24. The intermediate member 27 is then forced to rotate due to the engagement of the primary ramp 34 and primary boss 37. As the outer member 21 is lifted and the intermediate member 27 rotates as described above, the secondary boss 39 is in engagement with the secondary ramp 35. The inner member is restricted from rotating with the intermediate member 27 as it is fixed rotationally to the housing 11 and therefore the engagement of the secondary boss 39 and the secondary ramp 35 causes the inner member to be forced up in a distal direction away from the housing 11. The cap 12 can then be removed from the housing.

When the first axially inclined portion 30 has a gradient shallower in an axial direction than the gradient of the second axially inclined portion 40 as shown in FIG. 13 then the axial movement of the outer member 21 from pulling in a distal direction is greater than the axial of movement of the inner member. In this instance the axial force on the inner member 24 is greater than the axial force applied to the outer member 21. It can be appreciated that this can be the opposite way round and that the second axially inclined portion 40 could have a gradient shallower in an axial direction than the gradient of the first axially inclined portion. This would mean that as the outer member 21 is pulled from the housing 11 as described above, the axial movement of the outer member 21 causes an axial movement of the inner member which is greater than the axial movement of the outer member.

It can be appreciated that there a number of ways which would be known to a person skilled in the art to rotationally and axially couple two components to one another. Any combination of grooves, clips, bosses, formations and protrusions can be used to couple each component described above allowing either rotational movement, axial movement or neither depending on the requirements described above. It can also be appreciated that the lifting portions 20, 50 may be located on the outer member and the inner member and the axially-inclined portions 30, 40 may be located on the intermediate member 27 or any combination of the above. It can be considered that the outer member 21 and inner member 24 comprise the ramps and the intermediate member 27 comprises the protruding boss, one facing outwards towards the outer member and away from the central axis of the device, and another boss facing inwards towards the inner member and towards the central axis of the device, or any combination of the above which facilitates the mechanism described above.

The injection device 10 may comprise a holding portion 42 at one end of the axially-inclined portion 30 or the second axially-inclined portion 40 to engage with the lifting portion 20 or second lifting portion 50 to resist relative movement of the cap 12 and the housing 11 before use. It may be required that the cap is pushed in a proximal direction to release the lifting portion from the holding portion 42 before removal of the cap. An advantage of this is that premature removal of the cap is prevented, this feature may also prevent movement of particular components of the device during storage or transport which could damage the device.

Figure 14:
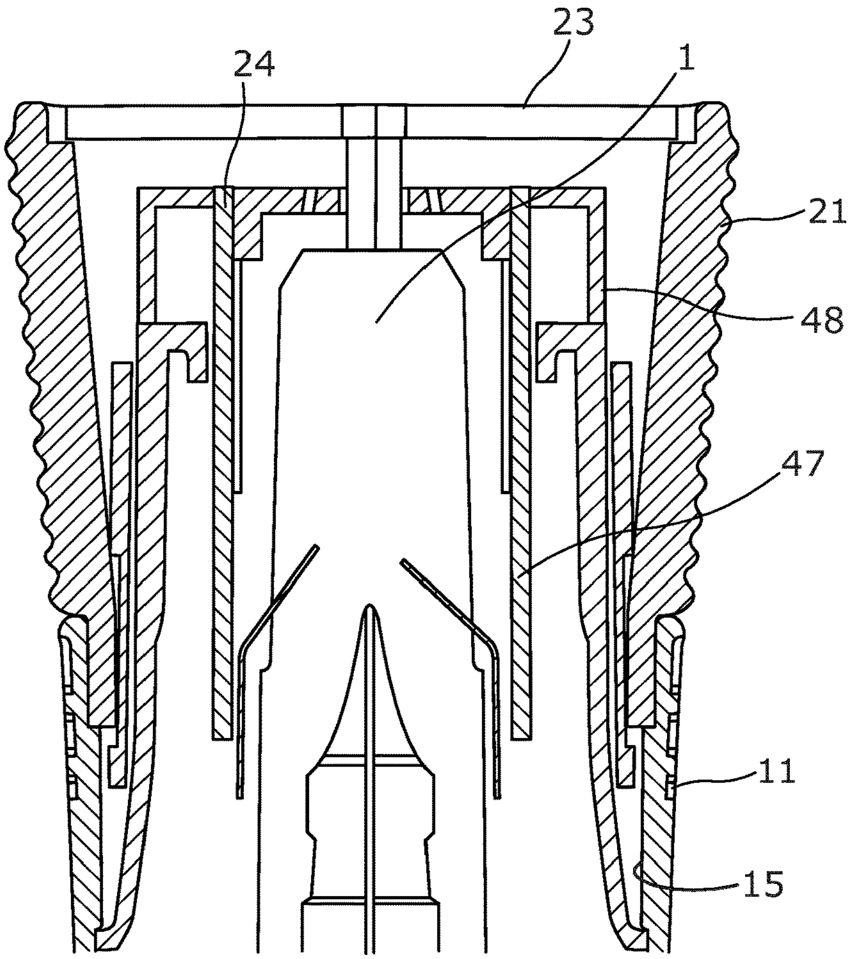
FIG. 14 is a cross-sectional side view of a cap according to a fourth embodiment.
Figure 15:
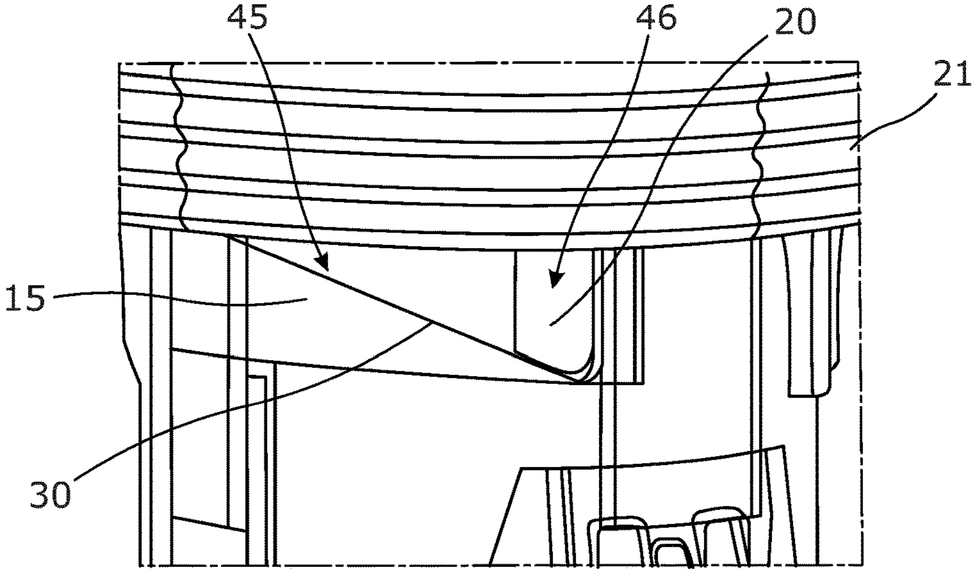
FIG. 15 is a close up view of the first lifting portion and axially-inclined portion of FIG. 14 with the housing showed as transparent so internal components can be seen.

Another embodiment is shown in FIGS. 14 and 15; a number of the features remain the same as previous Figures and like components retain the same reference numerals. In this aspect an inner wall 15 of the housing 11 comprises the axially-inclined portion 30, which in this aspect is an internal ramp 45. The lifting portion 20 being a proximally protruding boss 46, the boss 46 extends downwards from a proximal edge of the outer member 21 and in a proximal direction of the outer member 21. As the outer member is rotated the proximally protruding boss 46 engages with the internal ramp 45, lifting the outer member 21, the inner member 24 being fixed rotationally to the needle shield 1, but axially locked to the lid 23 and the outer member 21. Therefore the rotation of the outer member 21 and lid 23 allows the cap to be lifted and thus removed without rotation of the needle shield 1, needle sleeve or inner member 24. It can be appreciated that the inner member 24 can be made of two parts, an inner tube 47 and an outer tube 48. If coring, as described below is not an issue then the inner tube 47 can be integral or fixedly coupled to the outer member or lid. Furthermore it can be envisaged that the outer tube 48 may be rotatable with respect to the inner tube 47.

Figure 16:
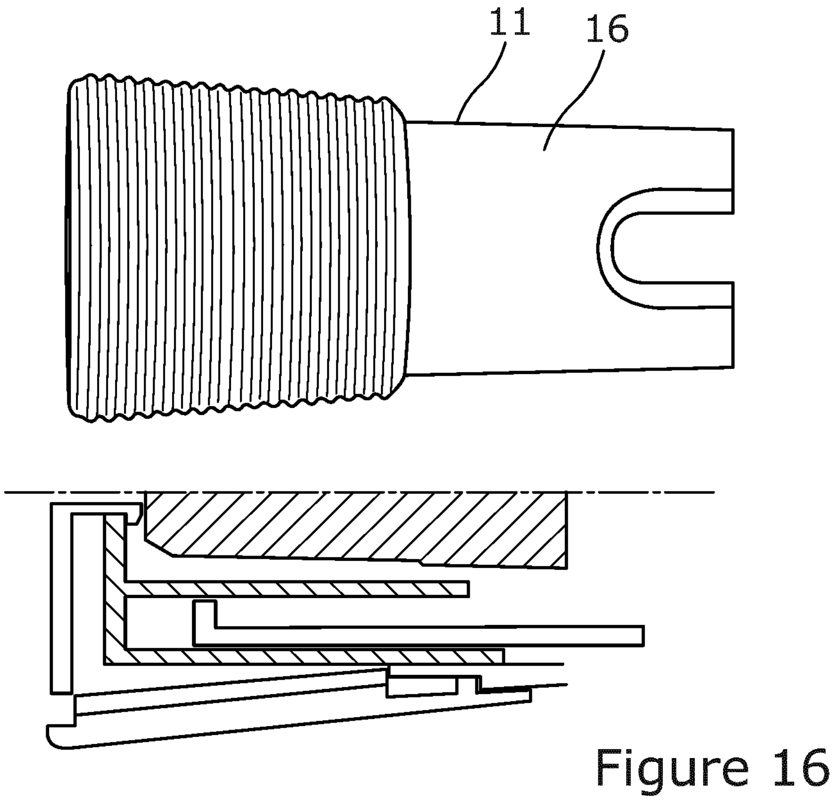
FIG. 16 is an alternative to FIG. 15 with the axially-inclined portion on an external face of the housing where the axially-inclined portion is visible both before and after uncapping.
Figure 17:
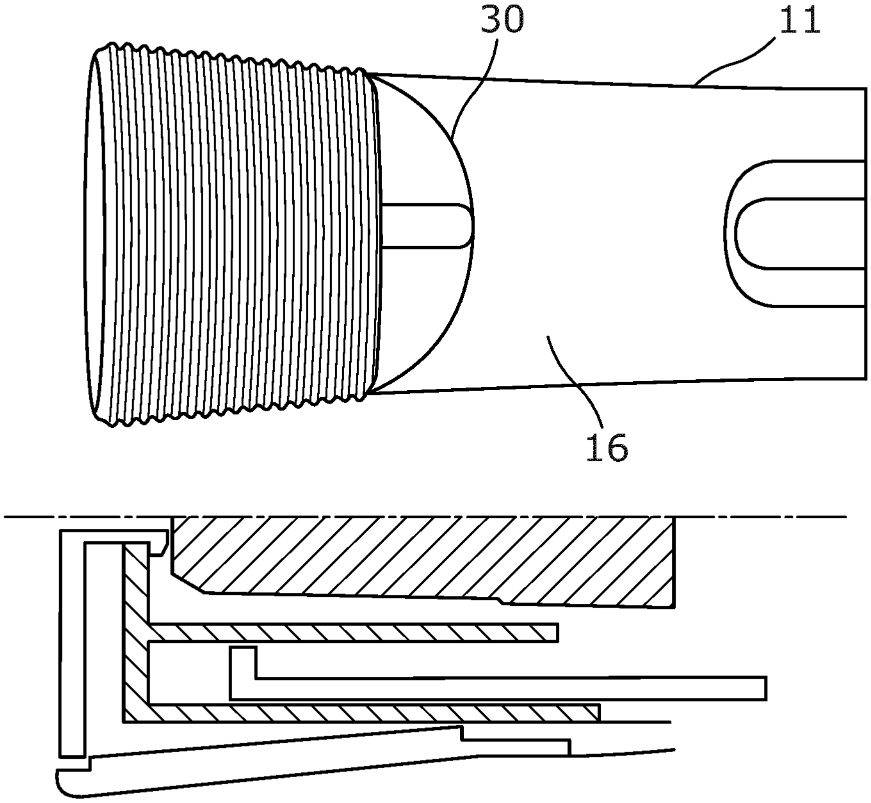
FIG. 17 is an alternative to FIG. 15 with the axially-inclined portion on an external face of the housing where the axially-inclined portion is not visible before uncapping.

It can be appreciated that the axially-inclined portion 30 described above can be disposed on an external face 16 of the housing as shown in FIG. 17, this enables the axially-inclined portion 30 to be visible both before and after uncapping (removing the cap from the injection device). Furthermore the axially-inclined portion 30 can be on the external face 16 of the housing however hidden by a longer length outer member 21 as in FIG. 16 extending further in a proximal direction than in other aspects. Wherein the axially-inclined portion 30 is concealed before the cap is removed from the injection device, however visible after the cap has been removed from the injection device.

It can be appreciated that the axially-inclined portion 30 is half-moon shaped, semicircular, linear with an incline in either direction, V-shaped or an alternative ramped shape. Any shape can be envisaged that would suitably enable a lifting portion to engage with it and to cause an inner member to be lifted in a distal direction as described in any aspect above as the outer member 21 is rotated or lifted. The lifting portion may be a protrusion extending inwardly, outwardly, proximally or distally of the central axis of the housing depending on the corresponding axially-inclined portion. The lifting portion and axially-inclined portion may be disposed on an inner surface or outer surface of the housing or the outer member.

The lifting portion is a protrusion on the outer member extending axially in a proximal direction from a proximal edge of the outer member, the axially-inclined portion being a recess or protrusion on the housing;

The lifting portion can be a protrusion on the housing extending axially in a distal direction from a distal edge of the housing, the axially-inclined portion being a recess or protrusion on the outer member;

The lifting portion can be an inwardly protruding boss on an inner surface of the outer member, extending towards the central axis of the housing, the axially-inclined portion being a recess or protrusion on the housing; and/or The lifting portion can be an outwardly protruding boss on an outer surface of the housing, extending away from the central axis of the housing, the axially-inclined portion being a recess or protrusion on the outer member.

Furthermore it can be appreciated that the lifting portion is on one of the housing 11 and the outer member 21 and the axially-inclined portion is on the other of the housing 11 and the outer member 21.

The lifting mechanism described above enables an interface between the outer member 21 and housing 11 which is non-circular in shape, for example but not limited to oval, rounded, square, or triangular shaped. This is due to the fact that the outer member 21 is lifted from the housing 11 as the outer member 21 rotates relative to the housing 11. This leaves the only contact between the outer member 21 and the housing 11 being the lifting mechanism.

It can be appreciated that any gradient or axially-inclined portion described in this specification could be also be non-constant. This would provide an advantage that the gearing the gradient provides can match the needle shield removal force which is also non-constant, i.e. in some embodiments as the cap is removed the force builds uniformly and then jumps to a peak. Therefore a variation in the gradients could provide gearing to provide low initial assistance to a user, followed by high assistance to a user to match the higher force required at the peak.

It can be appreciated that any lifting portion described in this specification can be for example but not limited to, a groove, clip, boss, formation, protrusion, cam or follower. It can be appreciated that any axially inclined portion described in this specification can be for example but not limited to a protrusion, an indent or groove or a cut out. The axially inclined portion is inclined; however it can be appreciated that it can incline in either direction, curve, or comprise more than one gradient. The lifting portion must be able to engage with the axially inclined portion to actuate axial movement from rotation, or actuate rotation from an axial movement.

It can be appreciated that the inner member of any embodiment described in this specification can be integral to the outer member or formed of two parts, an inner tube 47 and an outer tube 48, the inner tube 47 being integral to the outer member 21, where coring is not an issue. Coring is the damage of a needle 17 by rotation of the needle shield 1. The end of the needle 17 cuts a small portion of an inner surface of the needle shield 1 away as the needle shield 1 rotates with respect to the needle 17. As the needle shield 1 is then removed from the syringe 18 the cut portion can remain in the needle 17 blocking the needle 17 and damaging the injection device 10.

The injection device 1 may be disposable or it may be reusable.

The injection device 1 may provide a fixed dose or a user-settable dose.

The terms “drug” or “medicament” are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient (“API”), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about—4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

The invention claimed is:

1. An injection device comprising an elongate housing having a central axis and a cap provided at a distal end of the housing, the cap being removable from the housing, the injection device comprising a syringe received in the housing and comprising a needle shield, the cap comprising:

an outer member for a user to grip when removing the cap from the housing;

an intermediate member disposed substantially within the outer member, at least one of the intermediate member and the outer member being rotatable relative to the other of the intermediate member and the outer member; and an inner member disposed substantially within the intermediate member, the inner member being coupled to at least one of the outer member and the intermediate member, the inner member being configured to engage the needle shield of the syringe when the syringe is in the housing such that the inner member and intermediate member are removable together with the needle shield, wherein the injection device further comprises a lifting mechanism configured to reduce a force required to remove the cap and the engaged needle shield from the housing, the lifting mechanism comprising at least one axially-inclined portion in engagement with at least one lifting portion such that rotational movement of the outer member or the intermediate member is converted into an axial movement of the inner member in a distal direction from the housing, wherein the intermediate member comprises one of the axially-inclined portion and the lifting portion.

2. The injection device according to claim 1, wherein the outer member comprises a lid and a distal end of the inner member comprises an aperture in engagement with a fixing portion on the lid, such that the inner member is coupled to the lid so as to be fixed axially with respect to the lid and to be rotatable with respect to the lid.

3. The injection device according to claim 1, wherein the outer member comprises an annulus shaped portion in engagement with clips on a distal end of the inner member such that the inner member is fixed axially with respect to the outer member and rotatable with respect to the outer member.

4. The injection device according to claim 1, wherein the inner member is free to move axially in a distal direction with respect to the intermediate member until a first stop portion of the intermediate member engages with a second stop portion of the inner member such that the inner member is prevented from further axial movement relative to the intermediate member.

5. The injection device according to claim 1, wherein the at least one axially-inclined portion is a groove or a cut out and the lifting portion is a boss, wherein the lifting portion is located substantially within the at least one axially-inclined portion, wherein as the outer member is twisted the lifting portion is forced to follow a path of the at least one axially-inclined portion, causing axial movement of the outer member and the inner member in a distal direction.

6. The injection device of claim 1, wherein the at least one axially-inclined portion is a ridge or a projection and the lifting portion is a boss, wherein the lifting portion is axially offset from the at least one axially-inclined portion but in contact with a distal or proximal edge of the at least one axially-inclined portion, wherein as the outer member is twisted the lifting portion is forced to follow a path of the at least one axially-inclined portion causing axial movement of the outer member and the inner member in a distal direction.

7. The injection device according to claim 1, wherein the at least one axially-inclined portion is a first axially-inclined portion located on one of an outer face of the intermediate member and an inner face of the outer member, and the lifting portion is a first lifting portion on the other of the outer face of the intermediate member or the inner face of the outer member, the outer face being directed away from a central axis of the injection device and the inner face being directed towards a central axis of the injection device.

8. The injection device according to claim 7, wherein the lifting mechanism comprises a second lifting portion and a second axially-inclined portion, the second lifting portion being located on one of an inner face of the intermediate member and an outer face of the inner member and the second axially-inclined portion being on the other of the outer face of the inner member and the inner face of the intermediate member, the outer face being directed away from a central axis of the injection device and the inner face being directed towards a central axis of the injection device.

9. The injection device according to claim 8, wherein the second axially-inclined portion has a shallower gradient with respect to the axial direction than the first axially-inclined portion.

10. The injection device according to claim 7, wherein at least one of the first and second axially inclined portions is a groove or a cut out and at least one of the first and second lifting portions is a boss, wherein the at least one of the first and second lifting portions is located substantially within the at least one of the first and second axially-inclined portions, wherein as the outer member is lifted in a distal direction from the housing each of the first and second lifting portions is forced to follow a path of each of the first and second axially-inclined portion, causing rotational movement of the intermediate member and axial movement of the inner member.

11. The injection device according to claim 7, wherein at least one of the first and second axially-inclined portions is a ridge or a projection and at least one of the first and second lifting portions is a boss, wherein the at least one of the first and second lifting portions is axially offset from the at least one of the first and second axially-inclined portions but in contact with a distal or proximal edge of the at least one of the first and second axially-inclined portions, wherein as the outer member is lifted in a distal direction away from the housing each of the first and second lifting portions is forced to follow a path of each of the first and second axially-inclined portions, causing rotational movement of the intermediate member and axial movement of the inner member.

12. The injection device according to claim 8, comprising a holding portion at one end of the first axially-inclined portion or the second axially-inclined portion to engage with the first lifting portion, wherein when the holding portion and the first lifting portion are engaged, the cap and the housing are held together and relative movement of the cap and the housing is resisted.

13. The injection device according to claim 1, wherein the at least one axially-inclined portion comprises more than one gradient to provide varying levels of assistance in removal of the cap from the housing.

14. The injection device according to claim 1, wherein the at least one axially-inclined portion is in engagement with the at least one lifting portion such that rotational movement of the outer member or the intermediate member is converted into the axial movement of the inner member in the distal direction from the housing such that the axial movement of the inner member in the distal direction from the housing urges the engaged needle shield in the distal direction from the housing.

15. The injection device according to claim 1, wherein the needle shield comprises a rigid outer member and a resilient inner member.

16. The injection device according to claim 1, wherein the inner member is configured to engage the at least one of the outer member and the intermediate member.

17. The injection device according to claim 1, wherein the cap comprises the lifting mechanism.

18. The injection device according to claim 1, further comprising the syringe with the needle disposed within the housing, wherein the syringe contains a medicament.

19. The injection device according to claim 1, wherein the intermediate member is fixed axially to the inner member and not the outer member.

20. An injection device comprising:

an elongate housing having a central axis and a cap provided at a distal end of the housing, the cap being removable from the housing, the cap comprising an outer member for a user to grip when removing the cap from the housing; and an inner member disposed substantially within the outer member, the inner member being coupled to the outer member such that the outer member is rotatable with respect to the inner member, the inner member being configured to engage a needle shield of a syringe of medicament when such a syringe is received in the housing;

wherein the injection device comprises a lifting mechanism configured to reduce a force required to remove the cap and an engaged needle shield from the housing, the lifting mechanism comprising a lifting portion on one of the outer member and the housing, and an axially-inclined portion on the other of the outer member and the housing wherein, the lifting portion engages with the axially-inclined portion such that rotational movement of the outer member with respect to the housing is converted into an axial movement of the inner member in a distal direction from the housing, wherein the axially-inclined portion comprises more than one gradient to provide varying levels of assistance in removal of the cap from the housing.

* * * * *